United States Patent [19]
Dias

[11] Patent Number: 5,435,314
[45] Date of Patent: Jul. 25, 1995

[54] INTRAVASCULAR IMAGING CATHETER TIP HAVING A DYNAMIC RADIUS

[75] Inventor: J. Fleming Dias, Palo Alto, Calif.

[73] Assignee: Hewlett Packard Company, Palo Alto, Calif.

[21] Appl. No.: 218,005

[22] Filed: Mar. 25, 1994

[51] Int. Cl.⁶ .............................................. A61B 8/12
[52] U.S. Cl. .............................. 128/662.06; 128/660.1
[58] Field of Search ................ 128/660.03, 660.09, 128/660.1, 662.06

[56] References Cited

U.S. PATENT DOCUMENTS

| 5,005,185 | 3/1991 | Yock | 128/662.06 X |
| 5,107,844 | 4/1992 | Kami et al. | 128/662.06 |
| 5,320,106 | 6/1994 | Tanaka | 128/662.06 |

Primary Examiner—Francis Jaworski

[57] ABSTRACT

A catheter tip imaging probe varies the effective radius of resolution of an acoustic beam by translating the focal length. Varying the effective radius improves the resolution at any point of interest along the arterial walls. The focal length can be dynamically translated by deflecting either the transducer or the mirror in a conventional imaging probe.

13 Claims, 6 Drawing Sheets

INTRAVASCULAR IMAGING CATHETER TIP HAVING A DYNAMIC RADIUS

FIELD OF THE INVENTION

This invention is directed toward intravascular imaging, particularly towards improving resolution by dynamically varying the effective radius of resolution of a transducer.

BACKGROUND OF INVENTION

Cross-sectional scanning of arteries is performed by sweeping an acoustical beam repeatedly though a series of radial positions within a well-defined cross-sectional plane. The acoustic beam is swept by either a mechanically rotated acoustic element or electronically switched elements. For each radial position, the echoes, which contain physical information about the surrounding area, are sampled with the resulting values stored as lines in a scan converter memory. Each line corresponds to the radial position of the acoustic beam at the moment the echoes were created. Within the scan converter, the sampled echoes will be integrated to form a cross-sectional image of the artery. Using continual imaging techniques, the cross-section of the blood vessel and the lesion is displayed on a TV monitor. This image on the monitor, correctly displays the intima, media, adventitia, plaque, and in some cases the structure of the lesion.

Sweeping the acoustic beam is accomplished by either rotating a transducer or rotating a mirror. If the transducer is rotated, the shaft must be very flexible as it contains all of the electrical wires for the transducer. When the mirror is rotated, the non-moving transducer avoids the necessity of rotating electrical wires. However in each of these methods, the focal length of the acoustic beam is set, which leaves the best resolution at a fixed radius. This fixed radius may not correspond to the region of interest in the blood vessel.

Finer resolution is needed at different radii to better characterize the nature of a lesion. Unfortunately, as the transducer and the mirror are fixed in space, the focal length is also fixed. There are no provisions for dynamically changing the effective radius along the arterial wall. Vital information, which could lead to better treatment, is lost or degraded.

SUMMARY OF THE INVENTION

A catheter imaging probe varies the effective radius of resolution of an acoustic beam by translating the focal point. Varying the effective radius improves the resolution at any point of interest along the arterial walls. The focal point can be moved by dynamically translating either the transducer or the mirror in a conventional imaging probe.

DETAILED DESCRIPTION OF THE PREFERRED EMBODIMENT

Figure 1:
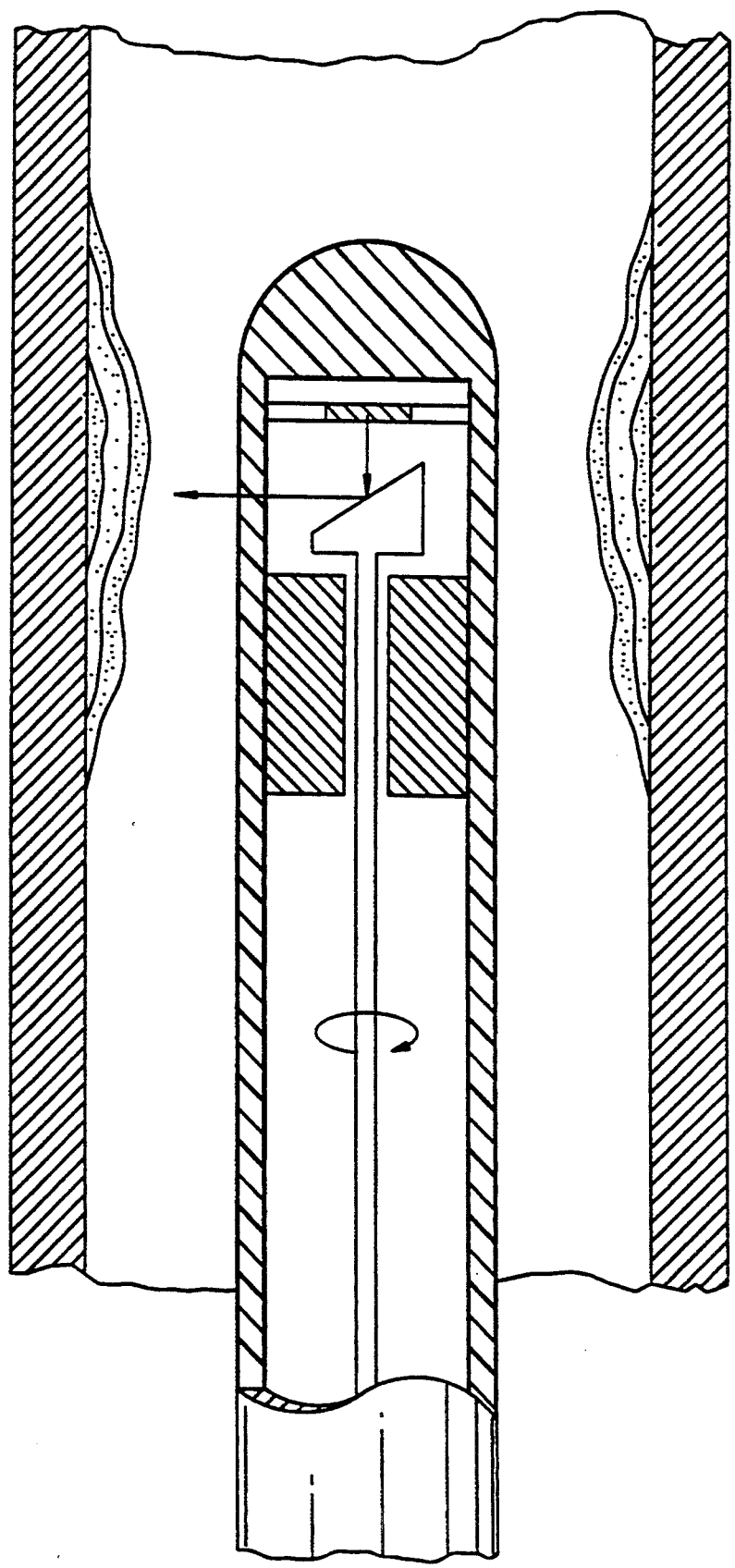
FIG. 1 illustrates a prior art probe.

FIG. 1 illustrates a probe of the prior art. The probe has a fixed radius of resolution. The best image resolution is along the fixed radius on the intravascular wall.

Figure 2:
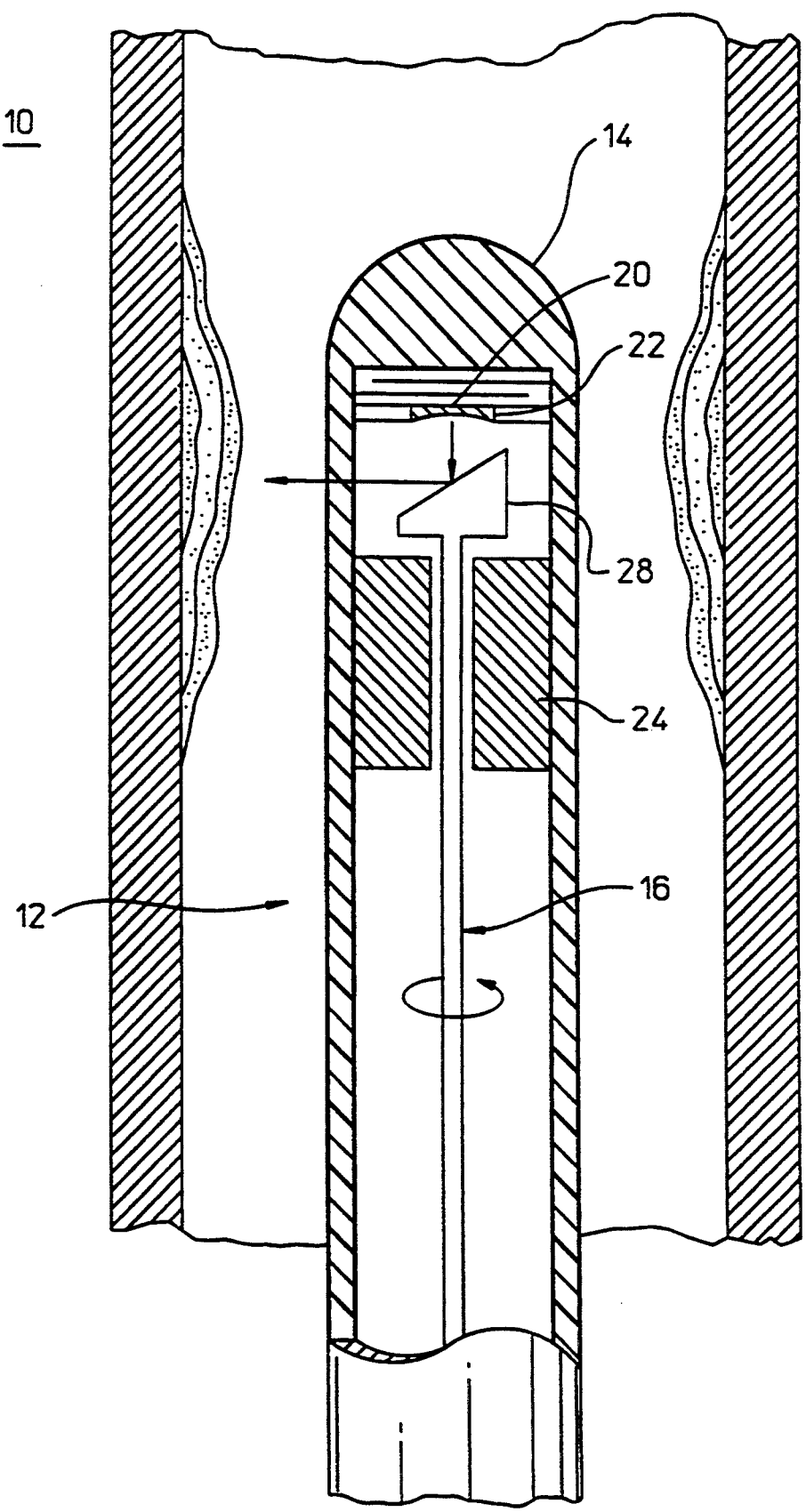
FIG. 2 illustrates a catheter imaging probe according to the present invention.

FIG. 2 illustrates an elegant embodiment of a catheter imaging probe 10 according to the present invention. The probe is shown within an artery. The radius of resolution can be dynamically varied in the catheter imaging probe 10. Electrical wires (not shown) are embedded throughout the length of the catheter tube 12. A catheter tip 14 is housed in the distal end of the catheter tube 12. A flexible shaft 16, connects to the catheter tip 14, extending through the tube 12 to an external control source (not shown).

At one end of the catheter tip 14, a rotatable mirror 18 connects to the flexible shaft 16. At the other end, an expanding plug 20 is attached to the distal end of the catheter tube 12 and is connected to the electrical wires (not shown). A transducer 22 is attached to the expanding plug 20. A sleeve bearing 24 secures the position of the end of the flexible shaft 16.

Thus, the mirror 18 has a fixed linear position with respect to the distal end of the catheter tube 12. When an electrical signal is applied to the expanding plug 20, the transducer 22 moves linearly and parallel to the axis of the flexible shaft 16 with respect to the distal end of the catheter tube 12. The parallel movement of the transducer translates the location of the focal point. The flexible shaft 16 provides rotational movement for the mirror 18. An example of suitable shaft rotating technology has been described in "Intravascular Ultrasound Imaging", edited by Jonathan Tobis and Paul Yock (1993), and "the Basics of Actuator Technology" by James West in Lasers & Optronics, September 1993. It will be apparent to those versed in the art that the mirror, alternatively, may be translated.

Figure 3:
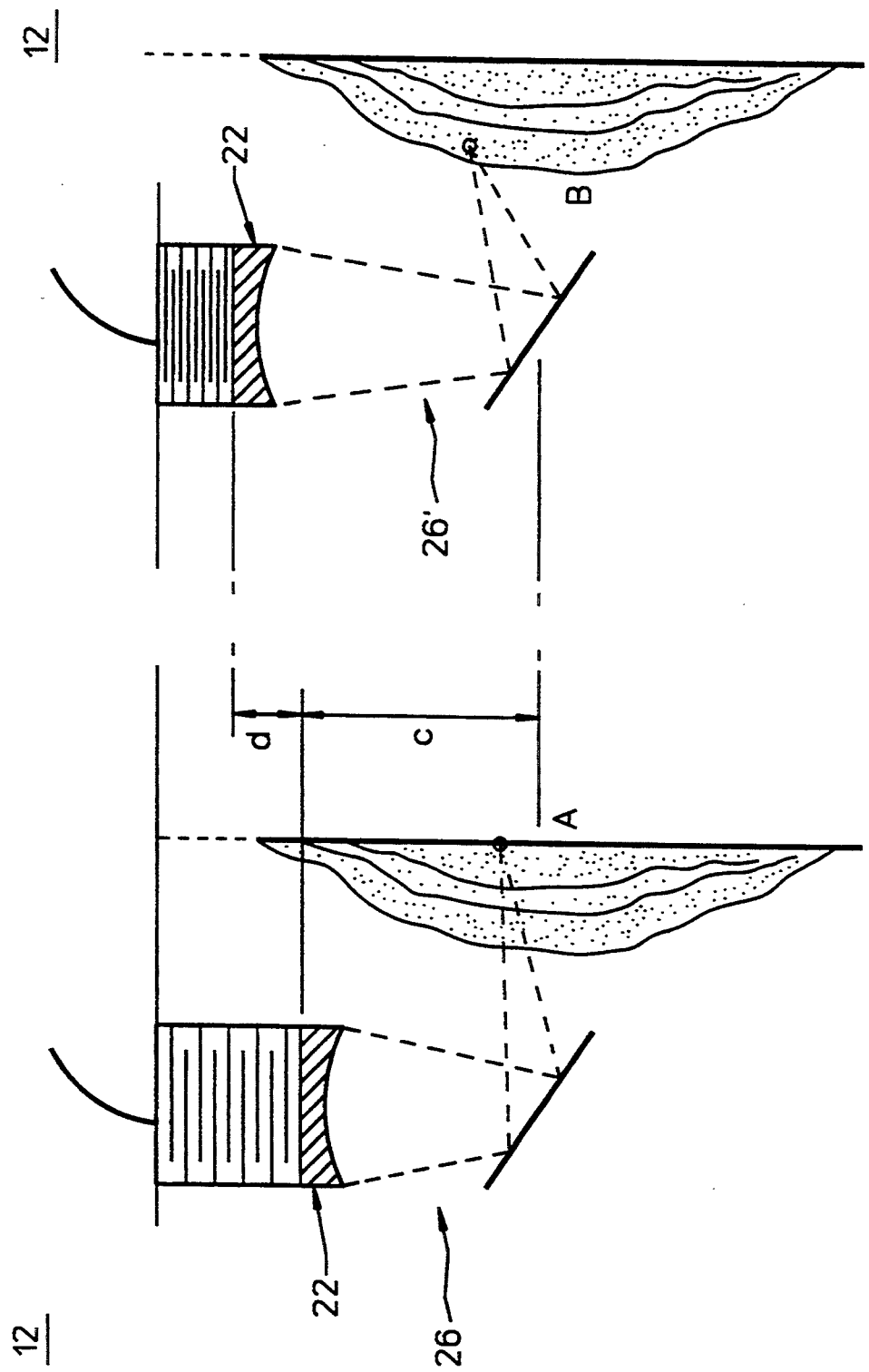
FIGS. 3A-B illustrate the operation of the catheter tip 14 shown in FIG. 2.

FIGS. 3A-B illustrates the operation of the catheter tip 14. In FIG. 3A, an acoustic beam 26, generated by applying an electrical signal to the transducer 22, is brought to a focus at point A. The back of the transducer 22 is initially a distance c from the mirror. The best resolution is within the adventitia of a lesion.

In FIG. 3B, the back of transducer 22 has been translated by an additional distance d. This translation results in a shifted acoustic beam 26'. When the focal point is moved from point A to point B, the best resolution is in the media of the lesion.

Figure 4:
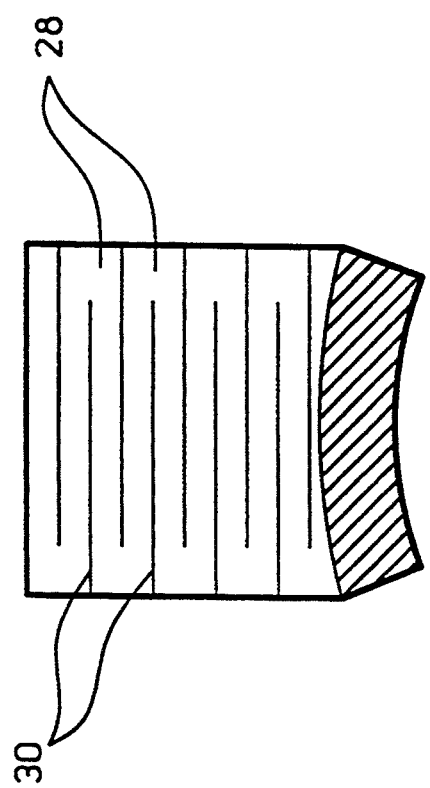
FIG. 4 illustrates a cross-sectional view of the expanding plug as shown in FIG. 2.

FIG. 4 illustrates a cross-sectional view of the expanding plug as shown in FIG. 2. The expanding plug 20 consists of multiple layers of electrorestrictive material 28. The electrostrictive layers 28 are separated by internal electrodes 30 which are alternately connected. When an electric field is applied across electrostrictive layers 28, the displacements are additive. The displacement is proportional to the square of the number of layers.

In one embodiment, the expanding plug is composed of lead magnesium niobate (PMN) with an additive of lead titanate. PMN is a relaxor ferroelectric. The properties and applications of relaxor ferroelectrics as actuators are described by Uchino et al. in the Journal of Materials Science, volume 16 (1981), pp. 569–578. The plug has ten layers of PMN where each layer has a thickness of 0.25 mm is described in that Journal. This provides a total compression of 25 microns when 200 volts are applied to the plug. The linear expansion may also be accomplished by attaching the mirror to an expanding plug. In this case, the PMN plug is powered from the proximal end, through slip rings since the shaft is rotating.

Other ways to shift the linear position of the transducer will become apparent to those having ordinary skill in the art. The movement could be provided by alternate means such as a tiny air bellow, a porous plug, an electromechanical activator, or a layered ceramic activator.

Figure 5:
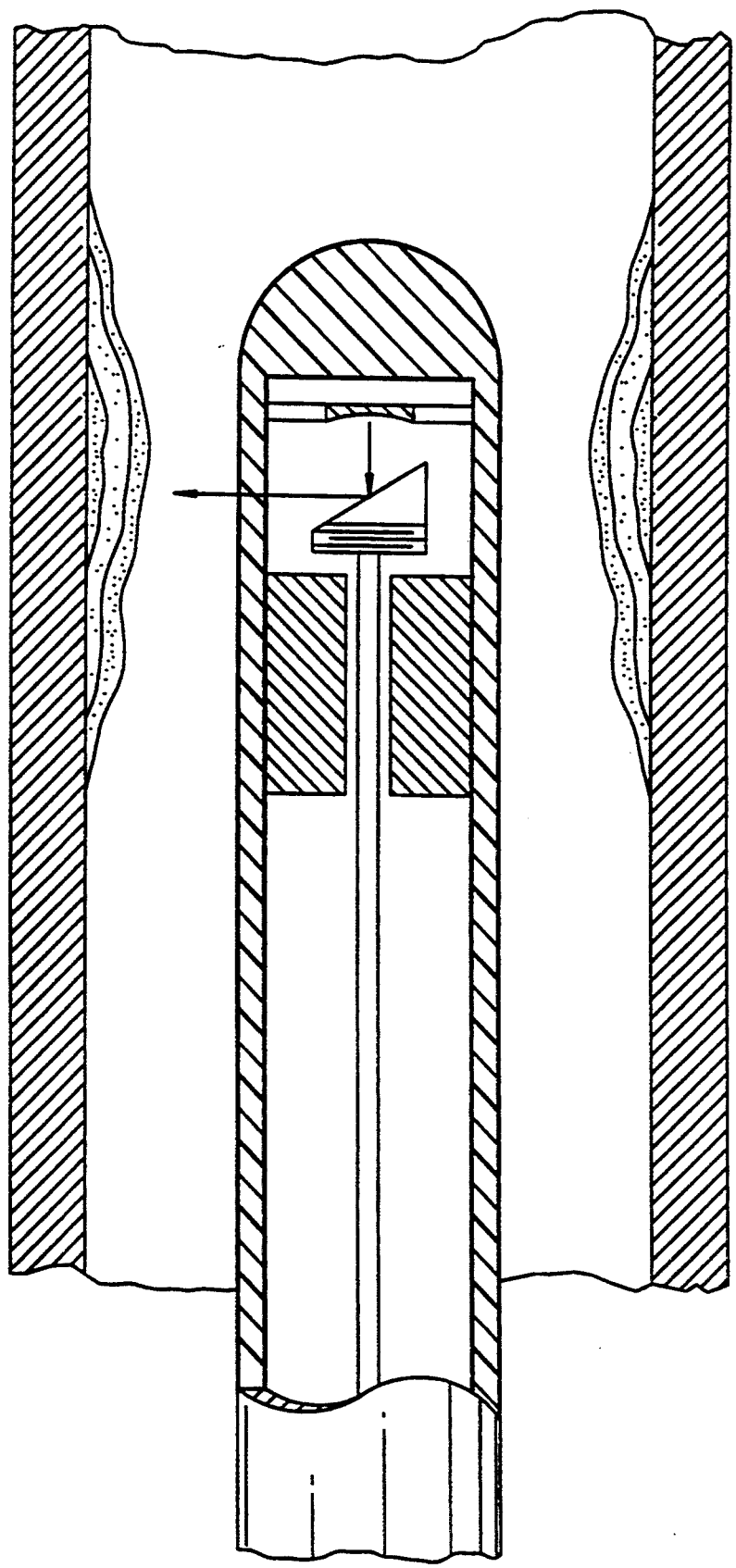
FIG. 5 illustrates a catheter imaging probe where the rotating mirror is shifted along the axis of the flexible shaft.

FIG. 5 illustrates a catheter imaging probe where the rotating mirror is shifted along the axis of the flexible shaft. The linear expansion may be accomplished by attaching the mirror to an expanding plug. In this case, the PMN plug is powered from the proximal end, through slip rings since the shaft is rotating.

Figure 6:
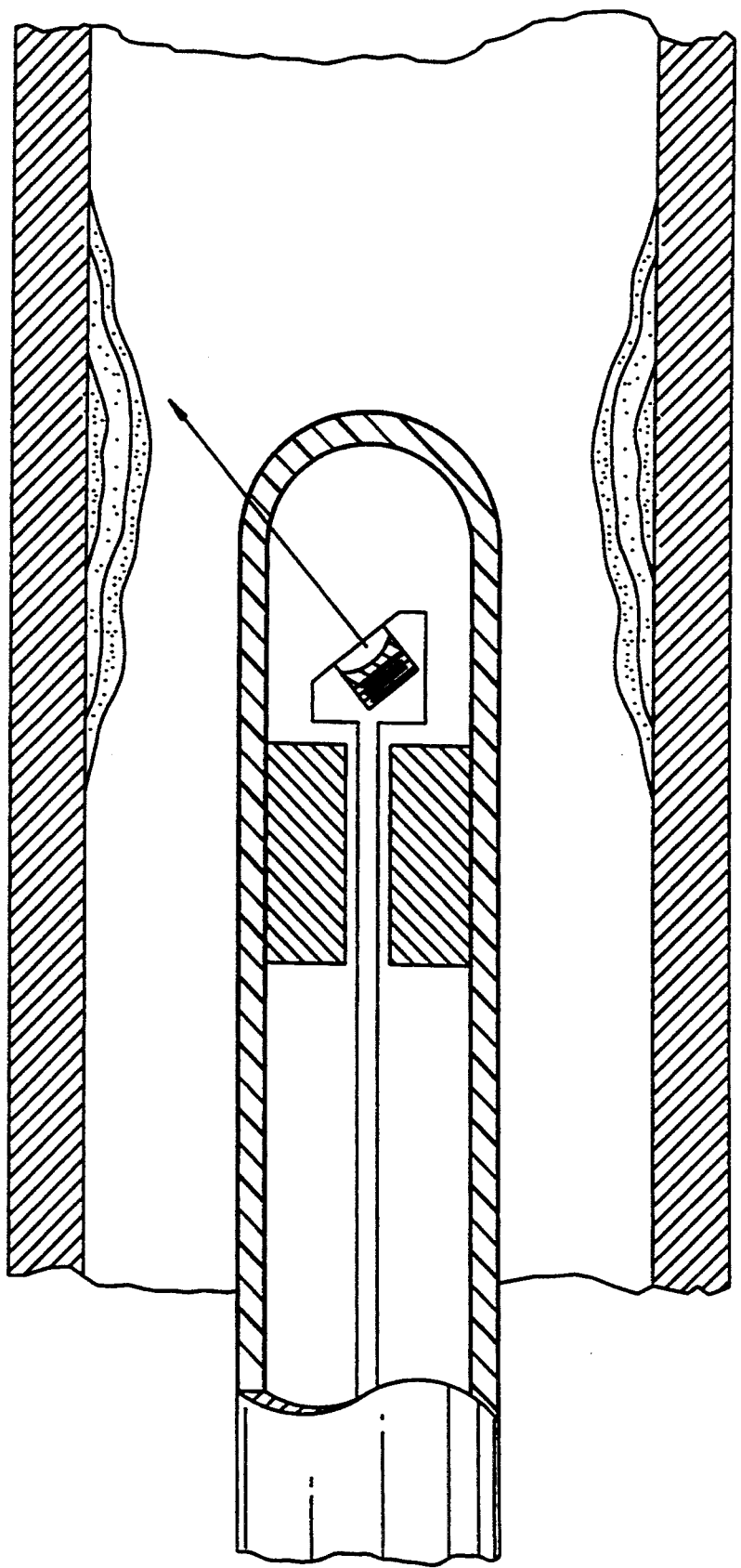
FIG. 6 illustrates a catheter imaging probe having a radially deflected transducer.

FIG. 6 illustrates the catheter imaging probe where the expanding plug is radially deflected. The plug is positioned between the transducer and the flexible rotating shaft. When a voltage is applied to the plug, the position of the transducer changes with respect to the axis of the flexible rotating shaft. Although the focal length remains unchanged, the focal point can be translated from a first radius of resolution to a second radius of resolution.

What is claimed is:

1. An intravascular imaging catheter tip comprising:
   catheter housing having a distal end;
   a transducer having a focal point that is positioned at a first radius of resolution, the transducer being attached to the distal end of the catheter housing, the transducer emitting a first acoustical wave in response to receiving a first electrical signal and sending a second electrical signal in response to receiving a second acoustical wave;
   transmission means for carrying the first and second electrical signals;
   a mirror receiving and deflecting the first and second acoustical waves;
   rotating shaft that rotates the first and second acoustical waves along a selected radius of resolution; and
   translating means, positioned within the distal end of the catheter housing, for shifting the focal point to a second radius of resolution by expanding and contracting.

2. An intravascular imaging catheter tip as defined in claim 1, further comprising:
   the translating means being positioned between the transducer and distal end, the translating means shifts the focal point from the first radius of resolution to the second radius of resolution by moving the transducer; and
   the rotating shaft being attached to the mirror.

3. An intravascular imaging catheter tip as defined in claim 2, wherein the translating means is a ferroelectric multilayer plug comprising:
   a back electrode attached to the distal end of the catheter housing;
   a series of ferroelectric layers extending from the back electrode to the transducer;
   a plurality of interleaving electrodes, each one interposing two adjacent ferroelectric layers; and
   a front electrode connecting between the series and the transducer;
   wherein the ferroelectric multilayer plug dynamically shifts the focal point by moving the transducer when an electric field is applied across the back, front and plurality of electrodes.

4. An intravascular imaging catheter tip as defined in claim 2, the translating means comprising a tiny air bellow.

5. An intravascular imaging catheter tip as defined in claim 2, the translating means comprising a porous plug.

6. An intravascular imaging catheter tips defined in claim 2, the translating means comprising an electromechanical actuator.

7. An intravascular imaging catheter tip as defined in claim 2, the translating means comprising a layered ceramic plug.

8. An intravascular imaging catheter tip as defined in claim 1, further comprising the translating means being positioned between the mirror and the rotating shaft, wherein the translating means shifts the focal point from the first radius of resolution to the second radius of resolution by moving the mirror along an axis parallel to the rotating shaft.

9. An intravascular imaging catheter tip as defined in claim 8, wherein the translating means is a ferroelectric multilayer plug comprising:
   a back electrode attached to the rotating shaft;
   a series of ferroelectric layers extending from the back electrode to the mirror;
   a plurality of interleaving electrodes, each one interposing two adjacent ferroelectric layers; and
   a front electrode connecting between the series and the mirror;
   wherein the ferroelectric multilayer plug dynamically shifts the focal point by moving the mirror when an electric field is applied across the back, front and plurality of electrodes.

10. A method of improving resolution of an intravascular imaging catheter tip having a transducer and a mechanical spring, the method comprising the steps of:
    projecting from the transducer an acoustic beam having a focal point at a first radius of resolution along an intravascular wall;
    changing the length of the mechanical spring;
    translating the focal point to a second radius of resolution along the intravascular wall; and
    receiving an image beam.

11. A method of improving resolution as defined in claim 10, wherein the step of translating the focal point comprises moving the transducer.

12. A method of improving resolution as defined in claim 10, wherein:
    the step of projecting further comprises projecting the beam onto a mirror; and
    the step of translating the focal point comprises moving the mirror linearly.

13. A method of improving resolution as defined in claim 10, wherein the receiving imaging beam is dynamically translated in time.

* * * * *